United States Patent
Baik et al.

(10) Patent No.: US 10,377,696 B2
(45) Date of Patent: Aug. 13, 2019

(54) METHOD AND APPARATUS FOR PURIFICATION OF DIMETHYL CARBONATE USING PERVAPORATION

(71) Applicants: POSCO, Pohang-si, Gyeongsangbuk-do (KR); ENERGY RESEARCH CENTRE OF THE NETHERLANDS, Le Petten (NL); RESEARCH INSTITUTE OF INDUSTRIAL SCIENCE & TECHNOLOGY, Pohang-si, Gyeongsangbuk-do (KR)

(72) Inventors: Joon-Hyun Baik, Pohang-si (KR); Jaap Ferdinand Vente, Alkmaar (NL); Anatolie Motelica, Alkmaar (NL)

(73) Assignees: POSCO, Pohang-si, Gyeongsangbuk-do (KR); NEDERLANDSE ORGANISATIE VOOR TOEGEPAST-NATUURWETENSCHAPPELIJK ONDERZOEK TNO, Da 'S-Gravenhage (NL); RESEARCH INSTITUTE OF INDUSTRIAL SCIENCE & TECHNOLOGY, Pohang-si, Gyeongsangbuk-do (KR)

( * ) Notice: Subject to any disclaimer, the term of this patent is extended or adjusted under 35 U.S.C. 154(b) by 0 days.

(21) Appl. No.: 15/539,008

(22) PCT Filed: Dec. 24, 2015

(86) PCT No.: PCT/KR2015/014252
§ 371 (c)(1),
(2) Date: Jun. 22, 2017

(87) PCT Pub. No.: WO2016/105156
PCT Pub. Date: Jun. 30, 2016

(65) Prior Publication Data
US 2017/0349530 A1 Dec. 7, 2017

(30) Foreign Application Priority Data

Dec. 24, 2014 (KR) .................. 10-2014-0189103

(51) Int. Cl.
*B01D 3/36* (2006.01)
*C07C 68/08* (2006.01)
*B01D 3/14* (2006.01)

(52) U.S. Cl.
CPC .............. *C07C 68/08* (2013.01); *B01D 3/145* (2013.01); *B01D 3/36* (2013.01)

(58) Field of Classification Search
CPC .......... B01D 3/145; B01D 3/36; C07C 68/08; C07C 69/96
See application file for complete search history.

(56) References Cited

U.S. PATENT DOCUMENTS

| | | | |
|---|---|---|---|
| 4,960,519 A | 10/1990 | Pasternak et al. | |
| 5,455,368 A | 10/1995 | Janisch et al. | |

(Continued)

FOREIGN PATENT DOCUMENTS

| | | |
|---|---|---|
| CN | 101143803 A | 3/2008 |
| CN | 201823480 U | 5/2011 |

(Continued)

OTHER PUBLICATIONS

International Search Report dated Apr. 8, 2016 issued in International Patent Application No. PCT/KR2015/014252.

(Continued)

*Primary Examiner* — Jonathan Miller
(74) *Attorney, Agent, or Firm* — Morgan Lewis & Bockius LLP

(57) ABSTRACT

An apparatus for separating dimethyl carbonate using pervaporation includes: an atmospheric distillation column and a high pressure distillation column distilling a mixture containing dimethyl carbonate and methanol and separating (Continued)

dimethyl carbonate from the mixture; and a pervaporation membrane module disposed between the atmospheric distillation column and the high pressure distillation column and allowing for permeation of the methanol to separate the methanol from the mixture, thereby reducing heat consumption and a process cost as compared to the case of only using an existing pressure swing distillation method.

6 Claims, 1 Drawing Sheet

(56) References Cited

U.S. PATENT DOCUMENTS

| | | | |
|---|---|---|---|
| 5,543,548 A | 8/1996 | Landscheidt et al. | |
| 6,899,743 B2 * | 5/2005 | Wijmans | B01D 3/145 210/640 |
| 9,334,228 B2 * | 5/2016 | Baik | C07C 68/00 |
| 2011/0144371 A1 * | 6/2011 | Ooms | B01D 3/009 558/277 |
| 2014/0051880 A1 * | 2/2014 | Baik | C07C 68/00 558/277 |

FOREIGN PATENT DOCUMENTS

| | | |
|---|---|---|
| CN | 103495342 A | 1/2014 |
| CN | 103772202 A | 5/2014 |
| DE | 4408697 A1 | 9/1995 |
| EP | 2679573 A1 | 1/2014 |
| EP | 2700629 A2 | 2/2014 |
| KR | 1995-0003251 A | 2/1995 |
| KR | 2008-0047916 A | 5/2008 |
| WO | 2014/002032 A1 | 1/2014 |

OTHER PUBLICATIONS

Hong-Mei Wei, et al., "Design and Control of Dimethyl Carbonate-Methanol Separation via Pressure-Swing Distillation," Industrial & Engineering Chemistry Research, Mar. 2013, vol. 52, No. 33, pp. 11463-11478.

J. Holtbruegge, et al., "Experimental investigation, modeling and scale-up of hydrophilic vapor permeation membranes: Separation of azeotropic dimethyl carbonate/methanol mixtures," Separation and Purification Technology, 2013, vol. 118, pp. 862-878.

Zhixian Huang, et al., "Novel Procedure for the Synthesis of Dimethyl Carbonate by Reactive Distillation," Industrial & Engineering Chemistry Research, Jan. 2014, vol. 53, No. 8, pp. 3321-3328.

Toshinori Tsuru, et al., "Pervaportion of Methanol/Dimethyl Carbonate Using SiO2 Membranes with Nano-Tuned Pore Sizes and Surface Chemistry," American Institute of Chemical Engineers, Aug. 2011, vol. 57, No. 8, pp. 2079-2089.

Extended European Search Report dated Dec. 21, 2017 issued in European Patent Application No. 15873683.5.

Z. Junliang, et al., "Process simulation for separation of dimethyl carbonate and methanol through atmospheric-pressurized rectification," Petrochemical Technology, vol. 39, No. 6, pp. 646-650 (with English Abstract).

Office Action issued in related Chinese Patent Application No. 201580070715.7 dated Nov. 28, 2018, with English translation.

* cited by examiner

[Fig. 1]
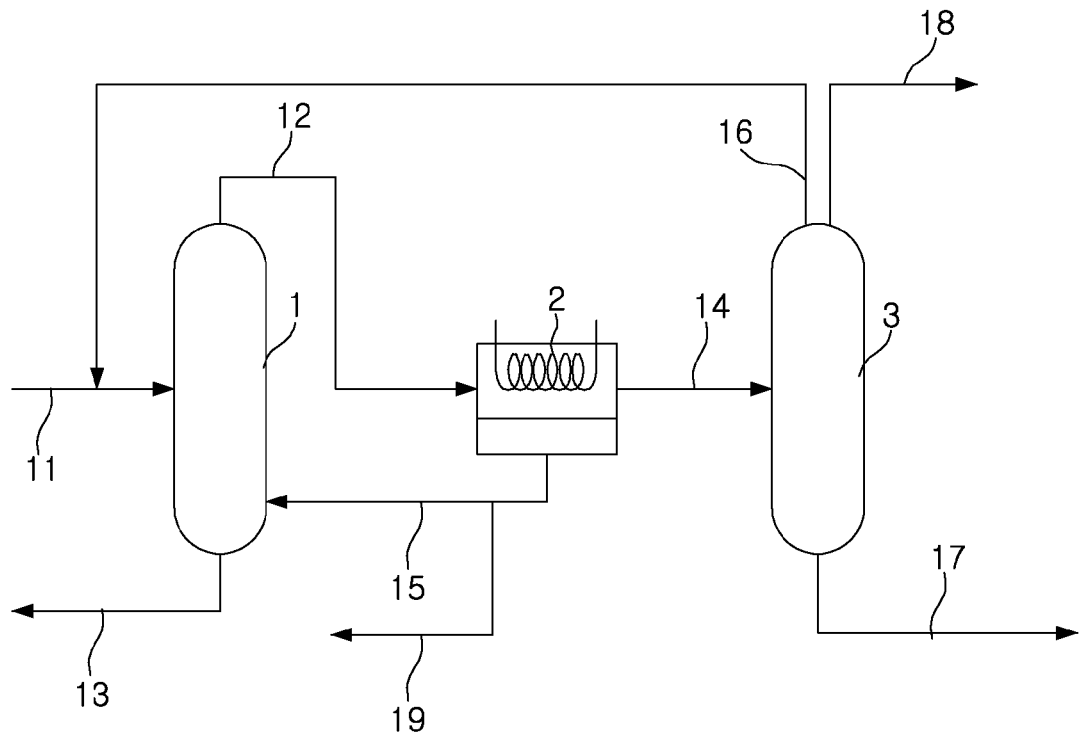
[Fig. 2]
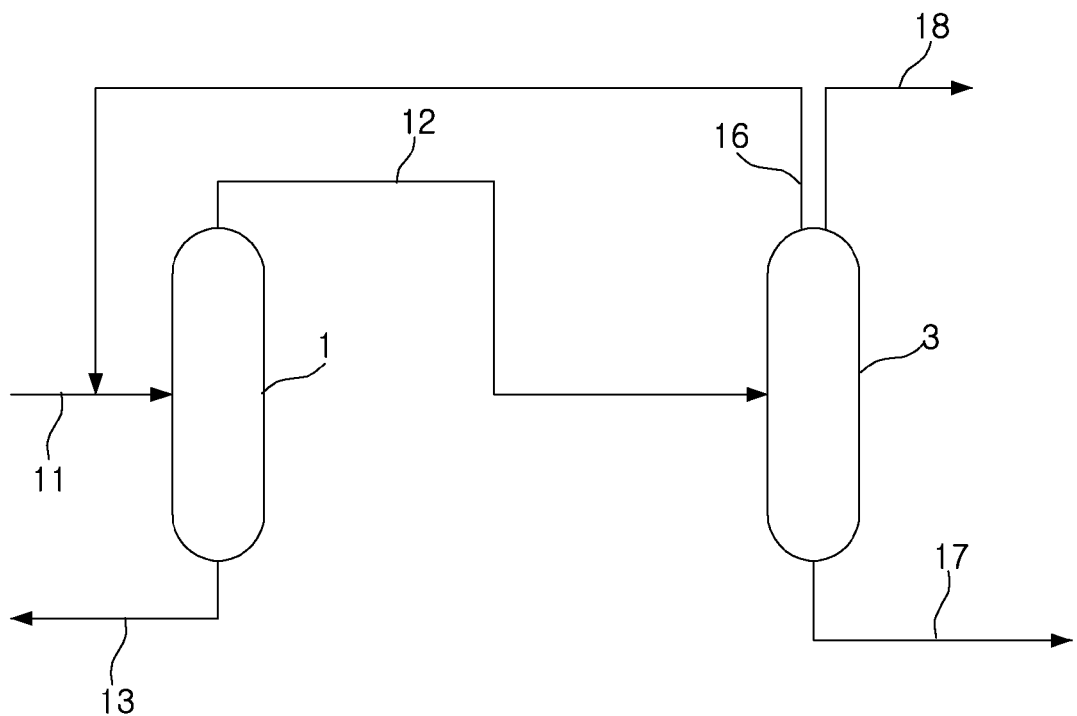

METHOD AND APPARATUS FOR PURIFICATION OF DIMETHYL CARBONATE USING PERVAPORATION

CROSS REFERENCE

This patent application is the U.S. National Phase under 35 U.S.C. § 371 of International Application No. PCT/KR2015/014252, filed on Dec. 24, 2015, which claims the benefit of Korean Patent Application No. 10-2014-0189103, filed on Dec. 24, 2014, the entire contents of each are hereby incorporated by reference.

TECHNICAL FIELD

The present disclosure relates to a method and apparatus for the purification of dimethyl carbonate using pervaporation.

BACKGROUND ART

Dimethyl carbonate is advantageously used as a starting material in the synthesis of a polycarbonate, a plastic engineering material, and is also advantageously used as a solvent and as a reactive material when producing various chemical products such as secondary battery electrolytes, and, paints. Dimethyl carbonate has been produced through a variety of methods, and among these methods, research into a method of producing dimethyl carbonate via a reaction between urea and methanol, in which relatively inexpensive raw materials are used, has been actively undertaken.

Relatively low concentrations of dimethyl carbonate, e.g. less than about 25% by weight, may often be present in a mixture with methanol. In particular, dimethyl carbonate can be obtained from a mixture thereof with methanol using a variety of methods for producing dimethyl carbonate. Dimethyl carbonate and methanol form an azeotropic composition having a dimethyl carbonate to methanol weight ratio of about 30:70 at atmospheric pressure.

Thus, high purity dimethyl carbonate, e.g. well over 99% by weight, is required to be separated from a mixture containing dimethyl carbonate and methanol. Since dimethyl carbonate and methanol form an azeotrope, the efficient separation thereof may not be obtained through a general separation process, and thus, a specific separation process is applied thereto. Here, for example, a pressure swing distillation method, a high pressure distillation method, and an extractive distillation method may be used.

The extractive distillation method is a method for separating a mixture component representing azeotropic behavior. In an extractive distillation process, an extractive distillation agent changes a degree of relative volatility of components of a mixture so as to form a sufficient volatility differential, such that an effective separation through distillation may be obtained. However, there is a problem in that an additional distillation process to re-separate the extractive distillation agent and dimethyl carbonate from each other is required, and such a process may result in a relatively low dimethyl carbonate recovery rate, and high energy consumption and high investment costs due to the application of multiple columns.

Meanwhile, in the case of the pressure swing distillation method, operating costs may be increased, based on high-pressure operations and large recycle streams leading to increased equipment sizes, and found to be uneconomical.

DISCLOSURE OF INVENTION

Technical Problem

An aspect of the present disclosure may provide a method and apparatus for purifying dimethyl carbonate using pervaporation in order to resolve a problem occurring in an existing azeotrope separation method using a dimethyl carbonate and methanol azeotrope.

Solution to Problem

According to an aspect of the present disclosure, an apparatus for purifying dimethyl carbonate using pervaporation may include: an atmospheric distillation column and a high pressure distillation column distilling a mixture containing dimethyl carbonate and methanol and separating dimethyl carbonate from the mixture; and a pervaporation membrane module disposed between the atmospheric distillation column and the high pressure distillation column and allowing for permeation of the methanol to separate the methanol from the mixture.

The atmospheric distillation column may supply an amount of the mixture recovered from an upper portion of the atmospheric distillation column to the pervaporation membrane module.

The pervaporation membrane module may supply the recovered mixture to the high pressure distillation column.

The pervaporation membrane module may supply a permeation material to the atmospheric distillation column.

The high pressure distillation column may supply an amount of the mixture recovered from an upper portion of the high pressure distillation column to the atmospheric distillation column.

The pervaporation membrane module may contain a membrane that transports methanol preferentially over DMC. The membrane may be selected from a silica membrane, a organic-inorganic hybrid silica membrane, a zeolitic membrane, and a polymeric membrane which comprises polyvinylalcohol, polyimide, chitosan, or mixtures thereof.

The permeate side of the pervaporation membrane module will be operated at a vacuum between 10 to 1,013 mbar.

The pervaporation membrane module may be maintained at a temperature within a range of 65 to 200° C.

The feed and retentate side of the pervaporation membrane module may be maintained at a level equal to 1 to 20 bars.

The atmospheric distillation column may be maintained at a level equal to 0.5 to 5 bars.

The high pressure distillation column may be maintained at a level equal to 5 to 20 bars.

According to an aspect of the present disclosure, a method of separating dimethyl carbonate from a mixture containing dimethyl carbonate and methanol using pervaporation may include: the supplying of the mixture, supplying a mixture containing dimethyl carbonate and methanol to an atmospheric distillation column and distilling the mixture; 20 to 40 weight %; recovering the mixture containing 20 to 40 weight % of dimethyl carbonate from an upper portion of the atmospheric distillation column; supplying a mixture containing 20 to 40 weight % of dimethyl carbonate to a pervaporation membrane module and allowing for permeation of the methanol to separate the methanol from the mixture; recovering a mixture containing 40 to 80 weight % of dimethyl carbonate from the pervaporation membrane module; the recovering of the mixture, supplying a mixture containing 40 to 80 weight % of dimethyl carbonate to a high pressure distillation column and distilling the mixture; and recovering a mixture containing 80 to 99.9 weight % of dimethyl carbonate from a lower portion of the high pressure distillation column.

The method of separating dimethyl carbonate may further include: recovering the mixture containing the dimethyl carbonate from an upper portion of the high pressure distillation column and supplying the recovered mixture to an atmospheric distillation column in a recirculation operation.

The method of separating dimethyl carbonate may further include: discharging a permeation material containing the methanol from the pervaporation membrane module and supplying the permeation material to an atmospheric distillation column in a recirculation operation.

Advantageous Effects of Invention

According to an exemplary embodiment in the present disclosure, a method and apparatus for separating dimethyl carbonate using pervaporation may be provided, thereby reducing heat consumption and process costs as compared to the case of using an existing pressure swing distillation method alone.

BRIEF DESCRIPTION OF DRAWINGS

FIG. 1 is a schematic block diagram of an apparatus for separating dimethyl carbonate according to an exemplary embodiment in the present disclosure.

FIG. 2 is a schematic block diagram of an apparatus for separating dimethyl carbonate used in comparative examples 1 and 2 with respect to the present disclosure.

BEST MODE FOR CARRYING OUT THE INVENTION

Hereinafter, embodiments of the present disclosure will be described in detail with reference to the accompanying drawings. The disclosure may, however, be embodied in many different forms and should not be construed as being limited to the embodiments set forth herein. Rather, these embodiments are provided so that this disclosure will be thorough and complete, and will fully convey the scope of the disclosure to those skilled in the art.

FIG. 1 is a schematic block diagram of an apparatus for separating dimethyl carbonate according to an exemplary embodiment in the present disclosure. With reference to FIG. 1, the apparatus for separating dimethyl carbonate may include an atmospheric distillation column 1, a pervaporation membrane module 2, and a high pressure distillation column 3.

In detail, the apparatus for separating dimethyl carbonate may include the atmospheric distillation column 1 and the high pressure distillation column 3 distilling a mixture containing dimethyl carbonate and methanol to separate the dimethyl carbonate and the methanol from each other; and the pervaporation membrane module 2 disposed between the atmospheric distillation column 1 and the high pressure distillation column 3 to allow for permeation of the methanol to separate the methanol from the mixture.

High purity dimethyl carbonate may be separated from a dimethyl carbonate-methanol azeotrope using an existing pressure swing distillation method, but a high heat capacity is required and an equipment capacity may need to be increased at the time of performing a recirculation process, thereby resulting in high initial investment costs. Thus, according to an exemplary embodiment in the present disclosure, a dimethyl carbonate separation process may be performed by combining a pervaporation method with an existing pressure swing distillation method, so that heat consumption and a process cost may be reduced as compared to a case in which the pressure swing distillation method is used alone.

In further detail, according to an exemplary embodiment in the present disclosure, a method of separating dimethyl carbonate from a mixture containing dimethyl carbonate and methanol using pervaporation is provided. The method may include; the supplying of the mixture, supplying a mixture containing dimethyl carbonate and methanol to an atmospheric distillation column and distilling the mixture; 20 to 40; recovering the mixture containing 20 to 40 weight % of dimethyl carbonate from an upper portion of the atmospheric distillation column; supplying a mixture containing 20 to 40 weight % of dimethyl carbonate to a pervaporation membrane module and allowing for permeation of the methanol to separate the methanol from the mixture; recovering a mixture containing 40 to 80 weight % of dimethyl carbonate from the pervaporation membrane module; the recovering of the mixture, supplying a mixture containing 40 to 80 weight % of dimethyl carbonate to a high pressure distillation column and distilling the mixture; and recovering a mixture containing 80 to 99.9 weight % of dimethyl carbonate from a lower portion of the high pressure distillation column.

The mixture containing methanol and dimethyl carbonate in a dimethyl carbonate production process may be supplied to the atmospheric distillation column 1 by a supply pipe 11 of the atmospheric distillation column, and here, separation of the mixture may be performed through distillation.

In addition, in the case in which the mixture separation is performed by the atmospheric distillation column 1, impurities contained in the mixture may be removed. For example, in a case in which dimethyl carbonate is produced in a process of using urea as a raw material, methylcarbamate, an unreacted material, may be additionally contained and present in the mixture. In a case in which separation of such a mixture is performed in the atmospheric distillation column 1, the unreacted material, methylcarbamate, may be separated and removed.

The atmospheric distillation column 1 may distill the mixture containing dimethyl carbonate, methanol and methylcarbamate to perform separation thereof, so that the mixture having an increased content of dimethyl carbonate may be recovered. In an upper portion of the atmospheric distillation column 1, the mixture containing 20 to 40 weight % of dimethyl carbonate may be recovered. On the other hand, in a lower portion of the atmospheric distillation column 1, condensed methanol may be discharged by a lower discharge pipe 13 of the atmospheric distillation column.

In detail, the atmospheric distillation column 1 may be maintained at a level equal to 0.5 to 5 bars, preferably between 0.8 than 2 bars, and most preferably between 0.9 and 1.1 bars. In the case of a pressure lower than 0.5 bars or higher than 5 bars, additional energy may be required.

An amount of the mixture recovered from the upper portion of the atmospheric distillation column 1 may be supplied to the pervaporation membrane module 2. The supply may be performed by an upper discharge pipe 12 of the atmospheric distillation column connected between the atmospheric distillation column 1 and the pervaporation membrane module 2.

The pervaporation membrane module 2 may include a membrane, and in the mixture having the increased content of dimethyl carbonate received by the pervaporation membrane module 2, methanol and a small amount of dimethyl carbonate contained in the mixture may permeate through the membrane of the pervaporation membrane module to be discharged through a permeation material discharge pipe so that the mixture containing methanol and a small amount of dimethyl carbonate may be separated, and subsequently, an amount of the mixture having permeated the pervaporation membrane module 2 may have an increased content of dimethyl carbonate.

An amount of the mixture supplied to the pervaporation membrane module 2 by the upper discharge pipe 12 of the atmospheric distillation column may contain 20 to 40 weight % of dimethyl carbonate, and the mixture recovered from the pervaporation membrane module may be discharged by a concentrate discharge pipe 14 and may be a mixture containing 40 to 80 weight % of dimethyl carbonate.

On the other hand, a permeation material, which contains methanol and a relatively small amount of dimethyl carbonate, may permeate the membrane, and the purity of the methanol is at least 90 weight %, preferably at least 93 weight % and more preferably 96 wt %. The permeation material may be discharged through the permeation material discharge pipe A 15, and the discharged methanol may be used as a raw material in a process of the present disclosure or reused in other processes. Also, the pervaporation membrane module may supply a permeation material to the atmospheric distillation column.

The membrane contained in the pervaporation membrane module 2 may transport methanol preferentially over DMC. The membrane may be include silica membrane, organic-inorganic hybrid silica membrane, zeolitic membranes, polymeric membrane, like polyvinylalcohol, polyimide, chitosan or mixtures thereof, but is not limited thereto.

The permeate side of the pervaporation membrane module will be operated at a vacuum between 10 to 1,013 mbar, preferably between 100 to 900 mbar, and most preferably between 200 to 600 mbar. For example, in a case in which the degree of vacuum is less than 10 mbar, energy consumption may be increased uneconomically, and in a case in which the degree of vacuum exceeds 1,013 mbar, evaporation may not be smoothly performed.

In more detail, a temperature of the pervaporation membrane module may be maintained at 65 to 200° C., preferably a temperature between 100 and 180° C., and more preferably a temperature between 120 and 150° C. In a case in which the temperature thereof is lower than 65° C., the driving force may be excessively reduced, and accordingly, the required area of membrane surface may be excessively increased. As a result energy consumption may increase to uneconomical levels. Moreover, in a case in which the temperature thereof exceeds 200° C., energy consumption may be increased uneconomically and selective permeation of a mixture may be degraded.

Preferably, the temperature of the high pressure distillation column 3 is equal to or at least more than 90% of the temperature on the retentate side of the pervaporation membrane module 2.

The feed and retentate side of the pervaporation membrane module may be maintained at a level equal to 1 to 20 bars, preferably between 5 and 15 bars. In order to keep the mixture on the feed and retentate side of the pervaporation membrane module in the liquid state, a pressure level equal to 1 to 20 bars will be applied. In the case of a pressure lower than 1 bar, methanol and a small amount of dimethyl carbonate may not be smoothly permeated, and in the case of a pressure higher than 20 bars, selective permeation of a mixture may be degraded.

Preferably, the pressure of the high pressure distillation column 3 is equal to or at least more than 90% of the pressure on the retentate side of the pervaporation membrane module 2.

An amount of the mixture recovered from the pervaporation membrane module 2 may be supplied to the high pressure distillation column 3 through the concentrate discharge pipe 14. An amount of the mixture supplied to the high pressure distillation column 3 may contain 40 to 80 weight % of dimethyl carbonate. When the mixture is distillated at a high pressure distillation column 3 to have separation occurring therein, a mixture containing 80 to 99.9 weight % of dimethyl carbonate may be recovered. The mixture containing high concentration dimethyl carbonate as described above may be recovered from a lower portion of the high pressure distillation column 3, and may be discharged by a lower discharge pipe 17 of the high pressure distillation column to the outside of a device so as to be used in a process in which dimethyl carbonate is required.

On the other hand, a mixture containing low concentration dimethyl carbonate, for example, 0.2 to 20 weight % of dimethyl carbonate, may be recovered from an upper portion of the high pressure distillation column 3, and the mixture containing low concentration dimethyl carbonate as described above may be supplied to the atmospheric distillation column 1 through an upper discharge pipe A 16 of the high pressure distillation column. The atmospheric distillation column 1 may distill the mixture supplied from the upper portion of the high pressure distillation column 3 and a mixture supplied thereto through the supply pipe 11 of the atmospheric distillation column 1 to be evaporated together, so as to recover a mixture containing high concentration dimethyl carbonate therefrom.

The high pressure distillation column may be maintained at a level equal to 5 to 20 bars, preferably between 6 and 15 bars, and most preferably between 7 and 10 bars. In the case of a pressure lower than 5 bars, a relatively large amount of dimethyl carbonate may be discharged to an upper portion of the high pressure distillation column to lower a recovery rate, and in the case of more than 20 bars, a relatively large amount of temperature may be further required.

According to another exemplary embodiment in the present disclosure, a method of separating dimethyl carbonate using pervaporation may be provided. In detail, the method of separating dimethyl carbonate according to another exemplary embodiment may include supplying an amount of a mixture containing 20 to 40 weight % of dimethyl carbonate to the pervaporation membrane module 2 to allow for permeation of methanol and thus separate the methanol from the mixture; and recovering a mixture containing 40 to 80 weight % of dimethyl carbonate from the pervaporation membrane module 2.

The method of separating dimethyl carbonate may further include supplying a mixture containing dimethyl carbonate and methanol to the atmospheric distillation column 1 to be distilled before azeotrope containing dimethyl carbonate and methanol is supplied to the pervaporation membrane module 2; and recovering an amount of the mixture containing 20 to 40 weight % of dimethyl carbonate from an upper portion of the atmospheric distillation column 1.

The method of separating dimethyl carbonate may further include supplying an amount of the mixture containing 40 to 80 weight % of dimethyl carbonate to the high pressure distillation column 3 to then be distilled after the mixture containing 40 to 80 weight % of dimethyl carbonate is recovered from the pervaporation membrane module; and recovering a mixture containing 80 to 99.9 weight % of dimethyl carbonate from a lower portion of the high pressure distillation column 3.

The method of separating dimethyl carbonate may further include recovering a mixture containing dimethyl carbonate from an upper portion of the high pressure distillation column 3 and supplying the recovered mixture to the atmospheric distillation column 1.

Description of Reference Numerals

1: Atmospheric Distillation Column
2: Pervaporation Membrane Module
3: High Pressure Distillation Column
11: Supply Pipe of Atmospheric Distillation Column
12: Upper Discharge Pipe of Atmospheric Distillation Column
13: Lower Discharge Pipe of Atmospheric Distillation Column
14: Concentrate Discharge Pipe
15: Permeation Material Discharge Pipe A
16: Upper Discharge Pipe of High Pressure Distillation Column A
17: Lower Discharge Pipe of High Pressure Distillation Column
18: Upper Discharge Pipe of High Pressure Distillation Column B
19: Permeation Material Discharge Pipe B

MODE FOR THE INVENTION

Hereinafter, the present disclosure will be described in more detail through detailed exemplary embodiments. Exemplary embodiments described below are provided by way of examples, and thus, a scope of the present disclosure is not limited thereto.

Embodiment 1

As illustrated in FIG. 1, an apparatus for separating high purity dimethyl carbonate had a pervaporation membrane module 2 including a membrane and disposed between an atmospheric distillation column 1 and a high pressure distillation column 3. In performing an azeotrope separation process, azeotrope of methanol and dimethyl carbonate produced using urea as a raw material was supplied to the atmospheric distillation column 1, and methyl carbonate, an unreacted material, was separated from the azeotrope and methanol was distilled therein. Thus, a mixture solution containing 30 weight % of dimethyl carbonate was recovered from an upper portion of the atmospheric distillation column 1, and the recovered mixture solution was supplied to the pervaporation membrane module 2.

Mixture solution at a temperature of 130° C., at pressure of 8 atmospheres, heated using a preheater, was supplied to the pervaporation membrane module 2 and a temperature of the pervaporation membrane module 2 was maintained at 130° C. using a heating medium. A degree of vacuum in methanol permeating through a membrane was maintained at a level equal to 600 mbar. Methanol permeating through the membrane included in the pervaporation membrane module 2 was discharged by the permeation material discharge pipe A 15, and was used as a raw material in equipment of the present disclosure through high concentration methanol. A concentrate (a mixture containing 60 weight % of dimethyl carbonate) not permeating through the membrane was recovered from the pervaporation distillation membrane module 2 and was subsequently supplied to the high pressure distillation column 3.

The high pressure distillation column 3 was maintained at a level equal to 8 bars and was used to distill and separate the received mixture. High purity dimethyl carbonate was obtained from a lower portion of the high pressure distillation column 3, and a mixture containing a low concentration dimethyl carbonate discharged from an upper portion of the high pressure distillation column 3 was supplied to the atmospheric distillation column 1 so as to be recirculated.

Embodiment 2

The apparatus of Embodiment 1 was installed, and the same separation method as that of Embodiment 1 was applied thereto. Embodiment 2 has a difference from Embodiment 1 in that only a portion of a mixture containing low concentration dimethyl carbonate discharged from an upper portion of the high pressure distillation column 3 is recirculated by upper discharge pipe of high pressure distillation column A 16.

Comparative Example 1

As illustrated in FIG. 2, an apparatus in which the apparatus of Embodiment 1 from which the pervaporation membrane module 2 was omitted was used. In the atmospheric distillation column 1, an azeotrope of dimethyl carbonate and methanol was supplied thereto and distilled to perform separation in the azeotrope. Thus, a mixture solution containing 30 weight % of dimethyl carbonate was recovered from an upper portion of the atmospheric distillation column 1 and was supplied to the high pressure distillation column 3. The high pressure distillation column 3 was maintained at a level equal to 14.2 bars and the received mixture was distilled and separated thereby. High purity dimethyl carbonate was obtained from a lower portion of the high pressure distillation column 3, and a mixture solution containing low concentration dimethyl carbonate discharged from an upper portion of the high pressure distillation column 3 was supplied to the atmospheric distillation column 1 to be recirculated.

Comparative Example 2

The apparatus of Comparative Example 1 was installed and the same separation method as that of Comparative Example 1 was used. Comparative Example 2 has a difference therefrom in that only a portion of a mixture containing low concentration dimethyl carbonate discharged from an upper portion of the high pressure distillation column 3 was recirculated by upper discharge pipe of high pressure distillation column A 16.

TABLE 1

|  | Reduction in Separation Costs (Relative Comparison) |
| --- | --- |
| Comparative Example 1 | — |
| Comparative Example 2 | 4% |
| Embodiment 1 | 28% |
| Embodiment 2 | 45% |

Table 1 illustrates reduction effects with respect to separation costs through the apparatuses of Embodiments 1 and 2 and Comparative Examples 1 and 2. It can be appreciated from Table 1 that in the case that dimethyl carbonate is separated in Embodiments 1 and 2, separation costs are significantly reduced.

While exemplary embodiments have been shown and described above, it will be apparent to those skilled in the art that modifications and variations could be made without departing from the scope of the present invention as defined by the appended claims.

The invention claimed is:

1. An apparatus for purifying dimethyl carbonate using pervaporation, comprising:
    an atmospheric distillation column and a high pressure distillation column distilling a mixture containing dimethyl carbonate and methanol and separating dimethyl carbonate from the mixture; and
    a pervaporation membrane module disposed between the atmospheric distillation column and the high pressure distillation column and allowing for permeation of the methanol to separate the methanol from the mixture;
    wherein the pervaporation membrane module supplies a recovered amount of the mixture to the high pressure distillation column, and wherein on a permeate side, the pervaporation membrane module is operated at a vacuum between 10 to 1,013 mbar,
    wherein the atmospheric distillation column supplies an amount of the mixture recovered from an upper portion of the atmospheric distillation column to the pervaporation membrane module,
    wherein the pervaporation membrane module supplies a permeation material to the atmospheric distillation column,
    wherein the high pressure distillation column supplies an amount of the mixture recovered from an upper portion of the high pressure distillation column to the atmospheric distillation column.

2. The apparatus of claim 1, wherein the pervaportion membrane module comprises a methanol selective membrane selected from a silica membrane, a organic-inorganic hybrid silica membrane, a zeolitic membrane, and a polymeric membrane which comprises a polyvinyl alcohol, polyimide, chitosan, or mixtures thereof.

3. The apparatus of claim 1, wherein the pervaporation membrane module is maintained at a temperature within a range of 65 to 200° C.

4. The apparatus of claim 1, wherein the feed and retentate side of the pervaporation membrane module is maintained at a level equal to 1 to 20 bars.

5. The apparatus of claim 1, wherein the atmospheric distillation column is maintained at a level equal to 0.5 to 5 bars.

6. The apparatus of claim 1, wherein the high pressure distillation column is maintained at a level equal to 5 to 20 bars.

* * * * *